(12) United States Patent
Ricciardi et al.

(10) Patent No.: US 6,291,171 B1
(45) Date of Patent: *Sep. 18, 2001

(54) KIT FOR THE NON-INVASIVE IDENTIFICATION AND COLLECTION OF DNA

(76) Inventors: Robert P. Ricciardi, 137 Forge Rd., Glenn Mills, PA (US) 19342; John R. De Phillipo, 100 S. Thurlow Ave., Margate, NJ (US) 08402

(*) Notice: Subject to any disclaimer, the term of this patent is extended or adjusted under 35 U.S.C. 154(b) by 0 days.

This patent is subject to a terminal disclaimer.

(21) Appl. No.: 09/302,623

(22) Filed: Apr. 30, 1999

Related U.S. Application Data

(63) Continuation of application No. 08/878,435, filed on Jun. 18, 1997, which is a continuation-in-part of application No. 08/558,840, filed on Nov. 15, 1995, now abandoned.

(51) Int. Cl.[7] .............................. C12Q 1/68; C12P 19/34; B65D 69/00; A61B 17/06; A45C 11/20

(52) U.S. Cl. .............................. 435/6; 435/91.2; 206/223; 206/232; 206/438; 206/549; 206/570; 206/572; 206/803

(58) Field of Search ....................... 435/6, 91.2; 206/223, 206/549, 570, 572, 438, 232, 803

(56) References Cited

U.S. PATENT DOCUMENTS 5,101,970 * 4/1992 Turner .................................. 206/223

* cited by examiner

Primary Examiner—W. Gary Jones
Assistant Examiner—Joyce Tung

(57) ABSTRACT

A non-invasive kit is provided for collecting and transporting DNA specimens from an individual for analysis or study. The kit contains swabs for harvesting DNA cells from the mouths of individuals and corpses. The kit consists of a rectangular panel having a center portion and two hinged members. The center portion is provided with a folded stand with apertures for holding swabs containing the DNA specimens. Bar coded envelopes are also provided for mailing to a depository.

7 Claims, 1 Drawing Sheet

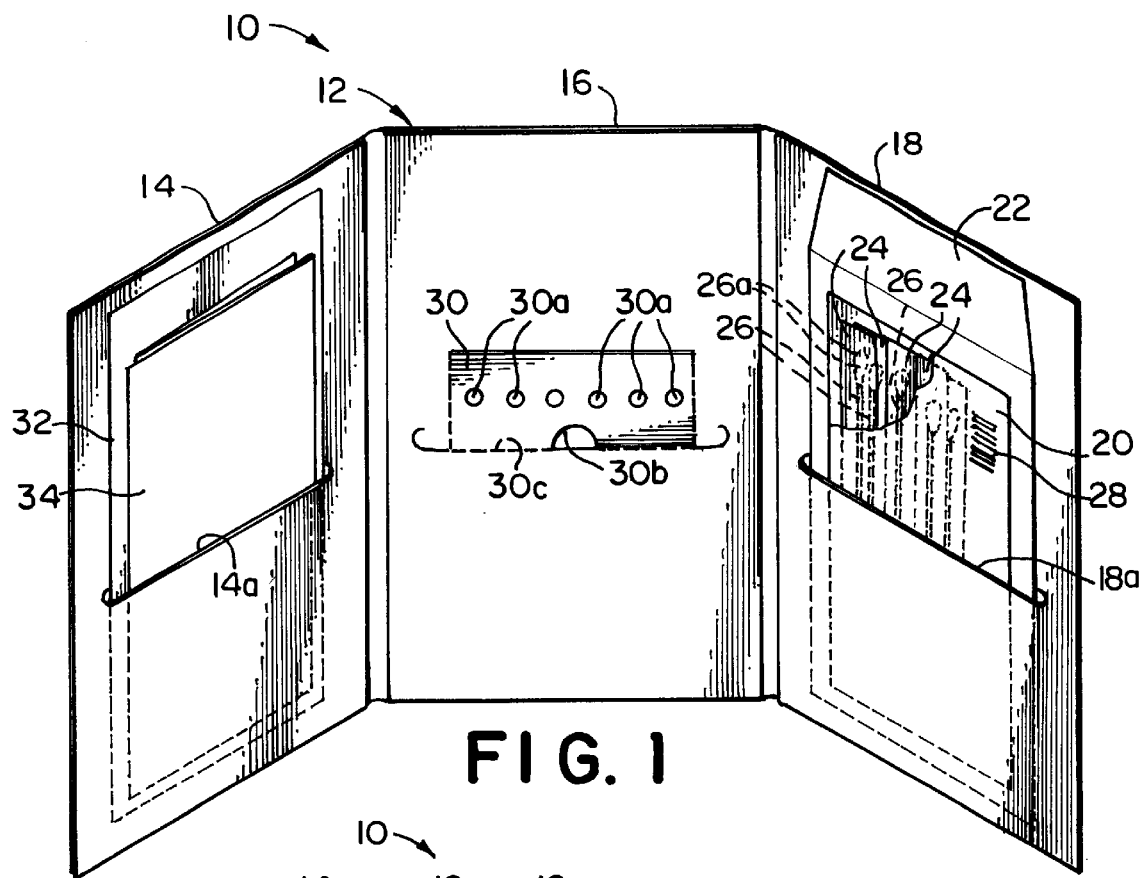
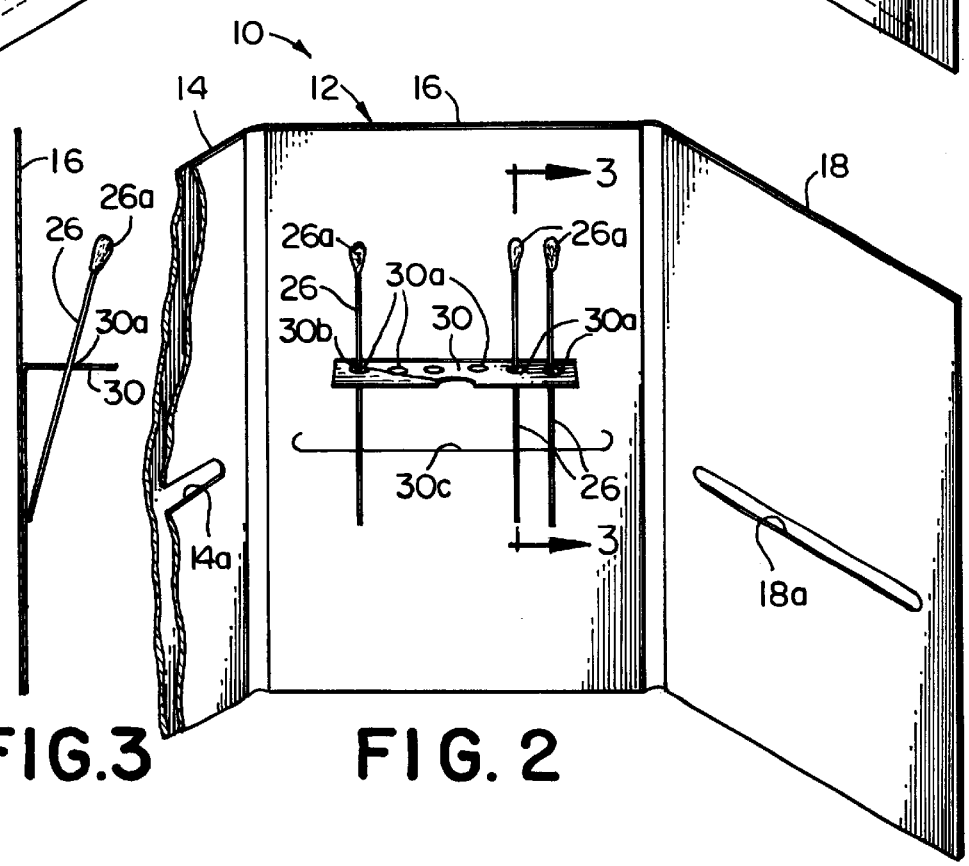
FIG. 1
FIG. 3  FIG. 2

KIT FOR THE NON-INVASIVE IDENTIFICATION AND COLLECTION OF DNA

RELATED APPLICATIONS

This application is a continuation of co-pending application Ser. No. 08/878,435 filed Jun. 18, 1997, which is a continuation-in-part of application Ser. No. 08/558,840 filed Nov. 15, 1995, now abandoned.

FIELD OF THE INVENTION

The present invention provides a kit for use in the home or by professionals for generating a genetic file for identification and medical evaluation. More particularly, the present invention relates to a kit for use in the harvesting of cells for DNA isolation and genetic testing from the mouths of individuals and corpses for the purpose of storage for later evaluation.

BACKGROUND OF THE INVENTION

The ability to diagnose genetic disease has developed rapidly over the last 20 years. There are tests today which could reveal to some the likelihood of suffering in later life diseases to which they have a propensity. Disease conditions with currently available tests include cystic fibrosis, Huntington's disease, Gaucher's disease, hemophilia, retardation, sickle cell anemia, Down's syndrome, and others.

While many gene-based applications are being used today in the diagnosis and prognosis of diseases, it is the area of predisposition testing that will provide the shift to disease prediction.

Information from parents and grandparents is seldom collected and preserved for use in genetic testing. DNA (deoxyribonucleic acid) matching has been used to identify missing people both living and dead.

The article of Richards et al. entitled, "Multiplex PCR Amplification From The CFTR Gene using DNA Prepared From Buccal Brushes/Swabs" *Human Molecular Genetics*, Vol. 2, No. 2, pps. 159–163 teaches the use of only two swabs in a professional atmosphere for screening genetic diseases and reports a failure rate of 5% in testing for the CFTR gene even when performed by health care professionals.

In many diseases, for example, prostatic cancers, it is recognized that there are three genes involved. Alzheimer testing involves at least four genes. It is further known that specific disease characteristics may be common for more than one disease. Therefore it is essential that a multiplicity of DNA samples are available in order to identify a disease. It is further essential that a large amount of DNA bearing material be stored because of degradation which can occur shortly before cryogenic storage. This is especially important since it may be impossible to obtain additional samples after the host has either disappeared or has been deceased for a long period of time.

Therefore, there exists a need for an effective system of collecting and preserving vital identifying or hereditary information about cell bearing specimens from family members. Such a system should be complete, convenient, easy to use at home without supervision and should be adapted to preserve cell bearing specimens for long periods of time without significant deterioration of the specimens.

U.S. Pat. No. 5,101,970 to Turner discloses one system for collecting and storing DNA specimens from living persons which includes storage of the specimens together with information in a freezer. However, the information is collected only from living parties and blood samples are used.

DNA is responsible for transmitting a person's hereditary characteristics. PCR (Polymerase Chain Reaction) technology can amplify a genetic blueprint a million fold as tiny segments of the human genomic DNA. DNA samples can be obtained by swabbing or scraping the inside of a cheek with a sterile swab.

DNA samples taken from skin or hair may be tainted with chemicals from hair sprays or body lotions so as to obscure the DNA reading.

It is understood that the term "inner cheeks" which is used herein refers to the cheek area as well as the portion of the mouth about the lips and is referred to as the buccal mucosa.

SUMMARY OF THE INVENTION

The present invention provides a kit for collecting and storing DNA bearing materials from living or deceased persons. According to the present invention, a plurality of sterile swabs are provided to collect the DNA bearing material from the inner cheeks of the person by stroking the inside of the cheeks at least about 10 times, preferably at least 20 times when unsupervised.

Advantageously, about 2250 nanograms of DNA bearing material is collected with each swab so as to obtain at least 4500 nanograms for preserving or testing.

The kit comprises a compartmented base member and a pair of hinged members which contain a client data information form and at least one mailing envelope having a bar code. A folded stand is formed in the kit, and a compartment for holding swabs for collecting oral buccal mucosa. The other compartments can also be provided to contain at least one mailing envelope and a client data sheet.

Advantageously, for use with corpses, there is provided means for detecting the presence of DNA on the swabs to ensure that a specimen has been obtained.

Also, for use with corpses, the swabs may comprise PCR so as to assure the fixing of the DNA.

It is thus an object of the invention to provide a convenient and non-invasive method of collecting DNA bearing specimens for identification.

It is another object to provide a kit for collecting DNA bearing specimens at home by non-professionals.

It is a further object of the invention to provide a kit for identification of persons killed in a common disaster such as a plane crash or during a war.

A further object of the invention is to provide loved ones with the peace of mind in knowing that should one of them become missing, a complete record for use in location and identification is readily available.

These and other objects, features, and advantages of the invention will become more apparent upon review of the following detailed description when taken in conjunction with the accompanying drawings.

BRIEF DESCRIPTION OF THE DRAWINGS

FIG. 1 is a perspective view of a kit embodying the present invention.

FIG. 2 is a similar perspective view showing the swab stand at a standing position.

FIG. 3 is side sectional view taken along line 3—3 of FIG. 2.

DESCRIPTION OF THE PREFERRED EMBODIMENTS

Referring to the drawings, the numeral 10 generally designates a collection and identification kit consisting of a generally rectangular panel having a base member 16 and a hinged member 14 on one side and a hinged member 18 on the other side. Preferably, the base member 16 is provided with a cut-out folded stand 30 having apertures 30a, which lies flat in the collection kit 10, but is able to be lifted by hand into a standing position. Base member 16 can also be provided with a compartment 30c for holding information sheets, swabs, or the like.

Hinge member 14 is normally provided with a client data information sheet 34 and a bar coded envelope 32 for mailing the data collection sheet to a depository for storage of the information.

Hinged member 18 can be provided with a compartment 18a which holds an envelope 22 having a bar code for mailing to either a storage facility or a testing laboratory. The bar code on envelope 22 is similar to the bar code on the envelope 32 to be sent to the depository, so that the depository is the only party having knowledge of the party being identified to maintain a confidentiality of the party.

Hinged member 18 may also contain a further envelope 20 having a bar code 28 which is similar to the bar codes on envelopes 32 and 22. Envelope 20 holds the swabs which were used to collect the DNA. Envelope 20 with the used swabs is inserted into envelope 22 for mailing to the storage or testing facility.

The kit 10 is also provided with packets 24 holding sterile swabs 26. Preferably, at least six swabs 26a are provided for each kit 10.

The swabs 26 contain heads 26a which are usually high modulus fibers such as dacron, which can successfully remove scrapings from the inner cheek. Where the party is a corpse, the swab heads 26a can comprise PCR or any other substance for fixing the DNA on the swab head.

As shown in FIG. 2, the stand 30 can be lifted by means of the cut-out 30b into a standing position prior to using the swabs 26. The stand 30 is provided with apertures 30a for holding the used swabs until they dry. The stand 30 is generally about 3 to 4 inches wide, preferably about 3½ inches wide, and about 1 to 2 inches, preferably about 1½ inches in height. Apertures 30a are provides which are spaced about ½ inch apart to hold the swabs at an angle as shown in FIG. 3. The apertures are generally about ¼ inch in diameter.

The swabs 26 are positioned in the apertures 30a at an angle so that they do not contact the surface. Following oral swabbing, the swab stand prevents the swab heads 26a which contain cells of the oral buccal mucosa from contacting any surface. This is critical since the polymerase chain reaction (PCR) which is eventually used to analyze the DNA extracted is very sensitive to contamination from other surfaces, for example a table or counter top.

The stand 30 also serves to keep track of each swab as it is used to collect cells of the oral buccal mucosa. In this manner, there is no confusion as to the number and which swabs have been used. In addition, the stand 30 assures that there is no mixing of swabs when two or more individuals are collecting DNA at the same time using separate kits.

It has been found that the drying of the swabs is important to prevent the growth of fungus. It is also for this reason that the envelopes containing the swabs should be water resistent. Depending upon the humidity in the place of use, it may be advisable to also insert into the mailing envelope a desiccant suitably encapsulated to keep the moisture content down.

The invention has been described above in terms of a preferred embodiment. It will be obvious, however, that many variations of the illustrated embodiment might well be contemplated by ordinarily skilled artisans. The order in which information and samples are taken and sealed can, for example, be different than that illustrated above. Further, various means for sealing the samples could also be used with results comparable to that of the sealable plastic envelopes of the preferred embodiment.

These and other modifications, deletions and additions might well be made to the illustrated embodiment without departing from the spirit and scope of the invention, as set forth in the claims.

What is claimed is:

1. A kit for the non-invasive collection and transporting of DNA specimens from an individual or a corpse for analysis or storage comprising:

a base member and a pair of hinged members, said base member having a cut-out portion having a plurality of apertures for holding swabs, said cut-out portion being bendable so as to form an upright stand to hold swabs in a drying position without contacting a contaminating surface, at least one of said members having a compartment containing at least two envelopes having a common bar code, and a plurality of swabs for collecting DNA samples from oral buccal mucosa from the mouth of the individual or corpse.

2. The kit according to claim 1 including a client information sheet.

3. The kit according to claim 1 wherein each member has a compartment.

4. The kit according to claim 1 wherein at least six swabs are provided.

5. The kit according to claim 1 wherein said swabs have swab heads of high modulus fibers.

6. The kit according to claim 1 wherein said swabs comprise swab heads with DNA polymerace.

7. Kits for the non-invasive collection and transportation of DNA specimens from corpses involved in a common disaster for analysis or storage, each of said kits comprising:

a base member and a pair of hinged members, said base member having a cut-out portion having a pularity of apertures for holding swabs, said cut-out portion being bendable to form an upright stand to hold swabs in a drying position without contacting a contaminating surface, at least one of said members having a compartment containing two envelopes having a common bar code which is different from the bar code of the other kits, and at least six swabs for collecting DNA samples from oral buccal mucosa from the mouth of the corpse, and an information sheet.

* * * * *